United States Patent
Chen

(10) Patent No.: US 11,951,122 B2
(45) Date of Patent: Apr. 9, 2024

(54) METHOD AND COMPOSITION FOR PREVENTING OR TREATING DIARRHEA, CONSTIPATION OR IRRITABLE BOWEL SYNDROME WITH FIBERS FORMED OF β-1-4-GLUCAN

(71) Applicant: Chao-Cheng Chen, Taipei (TW)

(72) Inventor: Chao-Cheng Chen, Taipei (TW)

(73) Assignee: Chao-Cheng Chen, Taipei (TW)

( * ) Notice: Subject to any disclaimer, the term of this patent is extended or adjusted under 35 U.S.C. 154(b) by 119 days.

(21) Appl. No.: 17/390,048

(22) Filed: Jul. 30, 2021

(65) Prior Publication Data

US 2022/0362281 A1 Nov. 17, 2022

(30) Foreign Application Priority Data

May 13, 2021 (TW) .................................. 110117272

(51) Int. Cl.
*A61K 31/716* (2006.01)
*A61K 9/00* (2006.01)
*A61K 45/06* (2006.01)
*A61P 1/12* (2006.01)
*C12P 19/04* (2006.01)
*C12R 1/02* (2006.01)

(52) U.S. Cl.
CPC .......... *A61K 31/716* (2013.01); *A61K 9/0053* (2013.01); *A61K 45/06* (2013.01); *A61P 1/12* (2018.01); *C12P 19/04* (2013.01); *C12R 2001/02* (2021.05)

(58) Field of Classification Search
None
See application file for complete search history.

(56) References Cited

U.S. PATENT DOCUMENTS

2019/0305158 A1* 10/2019 Korgel ................ H01L 31/0749

FOREIGN PATENT DOCUMENTS

| JP | 2014177437 A | * | 9/2014 | ........... A61K 31/717 |
| JP | 2019182704 A | * | 10/2019 | .............. B01J 20/20 |

OTHER PUBLICATIONS

De Bortoli, N., Martinucci, I., Bellini, M., Savarino, E., Savarino, V., Blandizzi, C., & Marchi, S. (2013). Overlap of functional heartburn and gastroesophageal reflux disease with irritable bowel syndrome. World journal of gastroenterology: WJG, 19(35), 5787. (Year: 2013).*

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*

* cited by examiner

*Primary Examiner* — Dale R Miller

(74) *Attorney, Agent, or Firm* — McCarter & English, LLP; Yu Lu

(57) ABSTRACT

Provided is a use of fibers formed of β-1-4-glucan in manufacturing a composition for preventing or treating diarrhea, constipation or irritable bowel syndrome, wherein the fibers have a diameter between 15 nm to 35 nm and a mean length of between 1.5 μm and 3.5 μm. Also provided is a method for preventing or treating diarrhea, constipation or irritable bowel syndrome with the fibers formed of β-1-4-glucan.

13 Claims, No Drawings

METHOD AND COMPOSITION FOR PREVENTING OR TREATING DIARRHEA, CONSTIPATION OR IRRITABLE BOWEL SYNDROME WITH FIBERS FORMED OF β-1-4-GLUCAN

1. REFERENCE TO RELATED APPLICATION

This application claims foreign priority under 35 U.S.C. § 119(a) to Patent Application No. 110117272, filed on May 13, 2021, in the Intellectual Property Office of Ministry of Economic Affairs, Republic of China (Taiwan, R.O.C.), the entire content of which Patent Application is incorporated herein by reference.

2. TECHNICAL FIELD

The present disclosure relates to compositions for preventing or treating diarrhea, constipation or irritable bowel syndrome, particularly to methods for preventing or treating diarrhea, constipation or irritable bowel syndrome by administering fibers formed of β-4-glucan.

3. DESCRIPTION OF RELATED ART

Irritable bowel syndrome, or IBS in short, refers to gastrointestinal functional intestinal disorders, such as repeated abdominal pain and discomfort accompanied by changes in bowel function, diarrhea, constipation, or a combination thereof. Symptoms usually last for a long period of time, and often for months or even years. Based on the condition of diarrhea or constipation, IBS can be divided into four types: (1) IBS with diarrhea (IBS-D); (2) IBS with constipation (IBS-C); (3) mixed type (IBS-M); and (4) unclassified IBS (IBS-U). Although irritable bowel syndrome is a common functional gastrointestinal disease, its cause remains unknown so far. Patients with irritable bowel syndrome may experience different symptoms such as diarrhea, constipation, abdominal pain, bloating, excessive gas, persistent urge to defecate, urgency to go to the toilet, incontinence, feeling of incomplete emptying, tension with bowel movements, hard or clumpy stools, or even inability to have bowel movements at all. Clinically, medications or supplements that can treat, relieve or prevent irritable bowel syndrome include stool volume increasing agents (such as dietary fibers), anti-diarrheal agents, laxatives, anti-intestinal spasm drugs, serotonin promoters or antagonists, anti-depressants, selective serotonin recovery inhibitors, antibiotics and probiotics. However, at present, the mechanism of medications or supplements on irritable bowel syndrome is not clear and has limited effects, and many even have side effects. For example, although tricyclic antidepressants can alleviate the symptoms of irritable bowel syndrome and relieve pain, they can cause side effects such as drowsiness and constipation. Although alosetron as a 5-hydroxytryptamine type 3 (5-HT3) receptor antagonist can reduce intestinal motility and relieve intestinal pain, it can produce side effects such as severe constipation and ischemic enteritis. Linaclotide and lubiprostone are used to treat the type of irritable bowel syndrome with constipation, but there are side effects of diarrhea. Therefore, the current use of various known medications or supplements must carefully evaluate patients' tolerance to side effects, and the dosage needs to be controlled or adjusted according to the actual condition of the patient, which leads to many inconveniences in the clinical setting.

Since the current medications used for irritable bowel syndrome have many side effects and elicit uncomfortable symptoms in patients treated for irritable bowel syndrome, physicians often need to spend more time in contemplating a prescription and dosing while diagnosing and treating patients for the syndrome due to the side effects of drugs on patients. Hence, there is still an urgent need to develop a safe and effective medication for treating, relieving or preventing irritable bowel syndrome.

SUMMARY

The present disclosure provides a use of a fiber made from β-1-4-glucan for manufacture of a composition for prevention or treatment of diarrhea, constipation or irritable bowel syndrome, wherein the fiber has a diameter of between 15 nm and 35 nm and a mean length of between 1.5 μm and 3.5 μm.

In at least one embodiment of the present disclosure, the irritable bowel syndrome is irritable bowel syndrome with constipation (IBS-C), irritable bowel syndrome with diarrhea (IBS-D), mixed irritable bowel syndrome (IBS-M), or unclassified irritable bowel syndrome (IBS-U).

In at least one embodiment of the present disclosure, the fiber has a length-to-diameter ratio of from 60 to 150.

In at least one embodiment of the present disclosure, the composition is administered at an effective amount for 1 to 4 times a day to individuals in need of prevention or treatment of diarrhea, constipation, or irritable bowel syndrome, and the composition for each administration is a freeze-dried tablet including 0.02 g to 0.12 g of the fiber. In at least one embodiment of the present disclosure, the composition may be administered to an individual in a form comprising fibers formed of β-1-4-glucan and a liquid medium, or the composition may be administered to an individual as a freeze-dried tablet.

In at least one embodiment of the present disclosure, the above-mentioned liquid medium is water.

In at least one embodiment of the present disclosure, the fiber is in a range of from 0.2% by weight to 1.2% by weight based on a total weight of the above-mentioned composition.

In at least one embodiment of the present disclosure, the composition comprises 0.1 mL of water with $OD_{620}$ between 0.25 and 1.25, such as between 0.4 and 1.22.

In at least one embodiment of the present disclosure, the fiber is formed by fermentation by at least one bacterium selected from the group consisting of *Gluconacetobacter, Acetobacter, Rhizobium, Sarcina, Pseudomonas, Achromobacter, Alcaligenes, Enterobacter, Azotobacter* and *Agrobacterium*.

In at least one embodiment of the present disclosure, the bacterium is at least one selected from the group consisting of *Acetobacter xylinum, Gluconacetobacter hansenii, Gluconacetobacter xylinus*, and *Gluconacetobacter sacchari*.

In at least one embodiment of the present disclosure, the composition further includes at least one selected from the group consisting of an organic nutrient, a probiotic, a drug, a dietary fiber, a flavoring agent, a dispersing agent, a wetting agent, a lubricant, a thickening agent, a stabilizer, a preservative, an antioxidant, an antibacterial agent and a coloring agent.

In at least one embodiment of the present disclosure, the composition is administered orally to an individual in need thereof.

The present disclosure also provides a method of prevention or treating diarrhea, constipation or irritable bowel syndrome, comprising administering to an individual in need a fiber formed of β-1-4-glucan, wherein the fiber has a diameter of from 15 nm to 35 nm and a mean length of between 1.5 μm and 3.5 μm.

In at least one embodiment of the disclosed method, the fiber is comprised in the composition and administered to an individual in need of prevention or treatment of diarrhea, constipation, or irritable bowel syndrome.

In at least one embodiment of the disclosed method, the composition may be administered to an individual in a form comprising fibers formed of β-1-4-glucan and a liquid medium, or the composition may be administered to an individual in a form of a freeze-dried tablet.

In at least one embodiment of the disclosed method, the liquid medium is water.

The present disclosure further provides a freeze-dried tablet comprising a fiber formed of β-1-4-glucan for prevention or treatment of diarrhea, constipation or irritable bowel syndrome, wherein the fiber has a diameter of between 15 nm and 35 nm and a mean length of between 1.5 μm and 3.5 μm.

In at least one embodiment of the disclosed method, composition and freeze-dried tablet, the irritable bowel syndrome is irritable bowel syndrome with constipation (IBS-C), irritable bowel syndrome with diarrhea (IBS-D), mixed irritable bowel syndrome (IBS-M), or unclassified irritable bowel syndrome (IBS-U).

In at least one embodiment of the disclosed method, composition and freeze-dried tablet, the fiber has a length-to-diameter ratio between 60 and 150.

In at least one embodiment of the disclosed method, composition and freeze-dried tablet, the fiber is administered 1 to 4 times a day to an individual in need of prevention or treatment diarrhea, constipation, or irritable bowel, and the composition for each administration includes 0.02 g to 0.12 g of the fiber.

In at least one embodiment of the disclosed method, composition and freeze-dried tablet, the fiber is in a range of from 0.2% by weight to 1.2% by weight based on a total weight of the composition.

In at least one embodiment of the disclosed method, composition and freeze-dried tablet, the composition comprises 0.1 mL of water with $OD_{620}$ between 0.25 and 1.25, such as between 0.4 and 1.22.

In at least one embodiment of the disclosed method, composition and freeze-dried tablet, the fiber is formed by fermentation of at least one bacterium selected from the group consisting of *Gluconacetobacter, Acetobacter, Rhizobium, Sarcina, Pseudomonas, Achromobacter, Alcaligenes, Enterobacter, Azotobacter* and *Agrobacterium*.

In at least one embodiment of the disclosed method, composition and freeze-dried tablet, the bacterium is at least one selected from the group consisting of *Acetobacter xylinum, Gluconacetobacter hansenii, Gluconacetobacter xylinus* and *Gluconacetobacter sacchari*.

In at least one embodiment of the disclosed method, composition, and freeze-dried tablet, the composition further comprises at least one selected from the group consisting of an organic nutrient, a probiotic, a drug, a dietary fiber, a flavoring agent, a dispersing agent, a wetting agent, a lubricant, a thickener, a stabilizer, a preservative, an antioxidant, an antibacterial agent and a coloring agent.

In at least one embodiment of the disclosed method, composition and freeze-dried tablet, the fiber is orally administered to an individual in need thereof.

The present disclosure effectively treats, improves, relieves, or prevents discomfort caused by diarrhea, constipation, and irritable bowel syndrome using fibers formed of β-1-4-glucan, and excellent effects with almost no side effects were observed.

DETAILED DESCRIPTION

The present disclosure is illustrated by the exemplary embodiments in the following. A person skilled in the art can easily conceive the other advantages and effects of the present disclosure, based on the disclosure of the specification. However, embodiments described in the specification are not intended to limit the scope of the present disclosure. The technical features or examples listed can be combined with each other. The present disclosure can also be carried out or applied in other different implementations. It is possible to modify or alter the disclosed examples for carrying out this disclosure without contravening its scope, for different aspects and applications.

As described herein, when "including," "comprising" or "having" specific elements is recited, unless otherwise specified, it may further include other elements such as components, structures, areas, parts, devices, systems, steps, or connecting relations, rather than excluding other elements.

As used herein, the singular forms "a," "an," and "the" include plural referents unless expressly and unequivocally limited to one referent. The term "or" is used interchangeably with the term "and/or" unless the context clearly indicates otherwise.

The numerical ranges described herein are inclusive and combinable. Any value falling within the numerical range described herein can be used as the maximum or minimum value to derive the secondary range; for example, "a diameter of between 15 nm to 35 nm" should be construed to include any sub-range between the minimum value of 15 nm and the maximum value of 35 nm, for example, 15 nm to 30 nm, 16 nm to 35 nm, and 22 nm to 28 nm; in addition, if a value falls within each range described herein (such as between the maximum value and the minimum value), it shall be deemed to be included in the scope of this disclosure.

In at least one embodiment of the present disclosure, the fiber formed of β-1-4-glucan has a diameter of 15 nm to 35 nm, for example, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm, about 30 nm, about 31 run, about 32 nm, about 33 nm, about 34 nm or about 35 nm. In some embodiments, the fibers of the present disclosure have a length of 1.5 μm to 3.5 μm, such as about 1.5 μm, about 1.6 μm, about 1.7 μm, about 1.8 μm, about 1.9 μm, about 2.0 μm, about 2.1 μm, about 2.2 μm, about 2.3 μm, about 2.4 μm, about 2.5 μm, about 2.6 μm, about 2.7 μm, about 2.8 μm, about 2.9 μm, about 3.0 μm, about 3.1 μm, about 3.2 μm, about 3.3 μm, about 3.4 μm or about 3.5 μm. In some embodiments of the present disclosure, the diameter of the fiber is between 15 nm and 35 nm, and the average length of the fiber is between 1.5 μm and 3.5 μm. In at least one embodiment of the present disclosure, the diameter of the fibers is between 15 nm and 35 nm.

The fiber formed of β-1-4-glucan in the present disclosure can be used for manufacture of a composition for prevention or treatment of diarrhea, constipation or irritable bowel syndrome, and can also be used for prevention or treatment of irritable bowel syndrome, comprising administering a fiber formed of β-1-4-glucan to an individual in need thereof. In some embodiments, the composition of the present disclosure may be a pharmaceutical composition, and is not limited thereto. In some embodiments of the present disclosure, the irritable bowel syndrome may be irritable bowel syndrome with constipation (IBS-C), irritable bowel syndrome with diarrhea (IBS-D), mixed irritable bowel syndrome (IBS-M), or unclassified irritable bowel syndrome (IBS-U).

In at least one embodiment, the fiber formed of β-1-4-glucan or the composition thereof in the present disclosure is in the form of a freeze-dried tablet, including a dosage form resulted from a freeze-drying process, such as in the form of a dry tablet. In some embodiments of the present disclosure, it can be processed by at least one of low-temperature freezing, air extraction under low temperature and low pressure, and desorption, so as to improve the overall stability of the product, and thus the product does not deteriorate easily. The excellent rehydration of the fiber thus prepared allows fast administration to the subject. In some embodiments of the present disclosure, the dosage form can be prepared through the sequential steps of low-temperature freezing, air extraction at low temperature and low pressure, and desorption. However, it should be understood that the sequence of the preparation steps is not limited thereto, and can be adjusted according to the desired features of the fiber. In some embodiments of the present disclosure, the fiber or its composition formed of β-1-4-glucan does not comprise a liquid medium, but in a form of dry powder prepared by a freeze-drying process, for example.

In at least one embodiment of the present disclosure, an individual in need of prevention or treatment of diarrhea, constipation or irritable bowel syndrome may directly take the fiber formed of β-1-4-glucan or the composition comprising the fiber orally in a form of, for example, oral freeze-dried tablets or dry powder, with no limitation. In some embodiments of the present disclosure, the fiber may be disintegrated in saliva in mouth and enter the gastrointestinal tract by swallowing.

In at least one embodiment of the present disclosure, when the freeze-dried or lyophilized tablet or dry powder is administered to an individual in need of prevention or treatment of diarrhea, constipation, or irritable bowel syndrome, the freeze-dried or lyophilized tablet or dry powder may be optionally mixed with a liquid medium first to form a composition comprising the liquid medium and fiber. In some embodiments, the individual's cough is avoided when the composition of the present disclosure comprising a liquid medium is taken orally, since the composition in a liquid state has good fluidity and is convenient for the individual to drink. In some embodiments of the present disclosure, the liquid medium may include edible liquids, such as water, juice, tea, etc., but is not limited thereto. In some embodiments of the present disclosure, since the prepared composition includes a liquid medium, the individual does not need to mix the fiber prepared by the present disclosure with a liquid medium before taking the composition of the present disclosure.

In at least one embodiment of the present disclosure, based on the total weight of the composition, the amount of fiber may be between 0.2% by weight and 1.2% by weight, so as to increase its dispersion rate. For example, the amount of fiber may be about 0.2% by weight, about 0.3% by weight, about 0.4% by weight, about 0.5% by weight, about 0.6% by weight, about 0.7% by weight, about 0.8% by weight, about 0.9% by weight, about 1.0% by weight, about 1.1% by weight, or about 1.2% by weight. In some embodiments of the present disclosure, when the amount of fiber is less than 0.2% by weight, the fiber may not provide enough hydroxyl groups, thereby affecting the interfacial tension of the liquid medium to some extent. In some embodiments of the present disclosure, when the amount of the fiber is less than 0.2% by weight, the liquid medium and the fiber may be agglomerated due to cohesive force, which leads to layering that hinders mixing.

In at least one embodiment of the present disclosure, when the amount of fiber in the composition is about 0.25% by weight, the liquid medium can be added in a single step or multiple steps. For example, the prepared fiber, the freeze-dried tablet or dry powder thereof is mixed with water or another liquid medium to form a liquid composition, with the freeze-dried tablet or dry powder disintegrated to form a liquid composition. In some embodiments of the present disclosure, a small amount of water or another liquid medium may be added first to make the fiber, freeze-dried tablet or dry powder form a thick liquid, and thereafter more water or liquid medium is added to further dilute the composition with better fluidity. For example, in some embodiments of the present disclosure, the amount of the fiber in the thick liquid formed in the first stage may be about 1.0% by weight, and after adding water or liquid medium one or more times, the content of the fiber may be between 0.1% by weight and 0.5% by weight. For example, it may be 0.1% by weight, 0.15% by weight, 0.2% by weight, 0.25% by weight, 0.3% by weight, 0.35% by weight, 0.4% by weight, 0.45% by weight or 0.5% by weight.

In at least one embodiment, the length-to-diameter ratio of the fiber prepared by the present disclosure may be between 60 and 150, e.g., 60, 65, 66, 67, 68, 69, 70, 75, 80, 85, 90, 95, 100, 105, 110, 115, 120, 125, 130, 135, 140, 141, 142, 143, 144, 145 or 150.

In at least one embodiment, the liquid composition formed by mixing the fiber and water prepared by the present disclosure may form a contact with the surface of the parafilm (Parafilm, Bemis, PM996) with an angle between about 95° to less than 110°, such as 95.5°, 96°, 96.5°, 97°, 97.5°, 98°, 98.5°, 99°, 99.5°, 100°, 100.5°, 101°, 101.5°, 102°, 102.5°, 103°, 103.5°, 104°, 104.5°, 105°, 105.5°, 106°, 106.5°, 107°, 107.5°, 108°, 108.5°, 109° or 109.5°.

In at least one embodiment, the optical density value ($OD_{620}$) measured at a wavelength of 620 nanometers (nm) for a composition comprising fiber at 0.2% to 1.2% by weight and 0.1 mL of water in the present disclosure is between 0.25 and 1.25. In some embodiments of the present disclosure, the lower limit of $OD_{620}$ may be 0.25, 0.26, 0.27, 0.28, 0.29, 0.3, 0.31, 0.33, 0.35, 0.37, 0.39, 0.4, 0.41, 0.43, 0.45, 0.5, 0.6, 0.7 or 0.8. In some embodiments of the present disclosure, the upper limit of $OD_{620}$ may be 1.25, 1.24, 1.23, 1.22, 1.21, 1.2, 1.1, 1, 0.9, 0.8, 0.7, 0.6 or 0.5. In some embodiments of the present disclosure, the value of the aforementioned $OD_{620}$ may be, for example, 0.295, 0.335, 0.435, 0.53, 0.54, 0.55, 0.65, 0.75, 0.76, 0.78, 0.85, 0.88, 0.93, 0.96, 0.98, 1.05, 1.08, 1.13, 1.14, 1.19, 1.215, or 1.225.

In at least one embodiment, the fiber of the present disclosure is obtained from biocellulose formed by one or more microorganisms through fiber separation procedures. The biocellulose can be formed from D-glucose linked with β(1→4) glycosidic bond to each other, therefore belonging to a β-1-4-glucan. In some embodiments of the present disclosure, biocellulose has higher purity unlike plant cellulose.

In at least one embodiment, the microorganisms disclosed in the present disclosure can be bacteria, and biocellulose can be produced by bacterial culture and fermentation. In some embodiments, the bacteria disclosed in the present disclosure may be at least one of the genus selected from the group consisting of *Gluconacetobacter, Acetobacter, Rhizobium, Sarcina, Pseudomonas, Achromobacter, Alcaligenes, Enterobacter, Azotobacter, Agrobacterium*, or any combination thereof. In some embodiments, the bacteria disclosed in the present disclosure may be at least one selected from the group consisting of *Acetobacter xylinum, Gluconacetobacter hansenii, Gluconacetobacter xylinus*, and *Gluconacetobacter sacchari*. In some embodiments of the present disclosure, *Gluconacetobacter xylinus* may be used to produce biocellulose, but it is not limited thereto. In some embodiments of the present disclosure, single bacterium or multiple bacteria can be used to produce biocellulose, and may be adjusted according to actual needs without limitation.

In order to provide the biocellulose for preparing the fiber of the present disclosure, a container containing a culture medium may first be allocated, and the aforementioned single bacterium or multiple bacteria may be cultured in the container containing the culture medium in a static manner for 24 to 96 hours (such as 24 hours, 36 hours, 48 hours, 60 hours, 72 hours, 84 hours, 96 hours). The absorbance (at a wavelength of 620 nm) of the bacterial concentration in the culture medium is controlled between 0.005 and 0.01, for example, about 0.005, about 0.006, about 0.007, about 0.008, about 0.009, or about 0.01. In some embodiments of the present disclosure, the pH value of the culture solution is controlled in an acidic environment, including between a pH of 0.5 and 6.5, for example, a pH of about 0.5, about 1.0, about 1.5, about 2.0, about 2.5, about 3.0, about 3.5, about 4.0, about 4.5, about 5.0, about 5.5, about 6.0 or about 6.5. In some embodiments of the present disclosure, the concentration of microorganisms in the culture medium is controlled in a range of between $10^2$ to $10^5$/mL, such as about $1\times10^2$/mL, about $5\times10^2$/mL, about $1\times10^3$/mL, about $5\times10^3$/mL, about $1\times10^4$/mL, about $5\times10^4$/mL or about $1\times10^5$/mL. In some embodiments of the present disclosure, the culture temperature may be controlled between 25° C. and 30° C., such as about 25° C., about 26° C., about 27° C., about 28° C., about 29° C., or about 30° C. In some embodiments of the present disclosure, the absorbance of the bacterial concentration in the culture medium, the pH value of the culture medium, the concentration of the microorganisms in the culture medium, the culture temperature or any combination thereof may be selected to control the culture of the microorganisms of the present disclosure.

As used herein, the term "static culture" refers to the formation of a fibrous membrane layer on the surface of the culture medium (i.e., the air-liquid interface) by bacteria in a non-woven manner. In addition, the container used for static culture can be a container with a wide and flat culture area, so as to regulate the oxygen consumption of bacteria with a lower container height, thereby modulating the diameter of the biocellulose formed. In some embodiments of the present disclosure, since the network structure formed by the biocellulose on the surface of the fiber membrane formed has a greater density and is more compact than the network structure inside the fiber membrane, the subsequent separation of interwoven biocellulose is facilitated by static culture and culture conditions disclosed by the present disclosure.

As used herein, the term "fibrous membrane" refers to a layered object that is interwoven with a plurality of biocelluloses and has a multi-layer network structure. In some embodiments of the present disclosure, the thickness of the fibrous membrane may be between 20 μm and 30 μm, such as about 20 μm, about 22 μm, about 24 μm, about 25 μm, about 26 μm, about 28 μm or about 30 μm. In some embodiments of the present disclosure, the amount of biocellulose per unit area of the fibrous membrane is between 0.001 g/cm$^2$ and 0.002 g/cm$^2$, such as about 0.0011 g/cm$^2$, about 0.0012 g/cm$^2$, about 0.0013 g/cm$^2$, about 0.0015 g/cm$^2$, about 0.0017 g/cm$^2$, about 0.0018 g/cm$^2$, or about 0.0019 g/cm$^2$. In some embodiments of the present disclosure, the diameter of the biocellulose in the fibrous membrane is between 15 nm and 100 nm, such as about 15 nm, about 20 nm, about 25 nm, about 30 nm, about 35 nm, about 40 nm, about 45 nm, about 50 nm, about 55 nm, about 60 nm, about 65 run, about 70 nm, about 75 nm, about 80 nm, about 85 run, about 90 nm, about 95 nm or 100 nm.

In at least one embodiment, the ingredients of the culture medium may include a carbon source, a nitrogen source, and a gel support, wherein the carbon source may include at least one sugar or sugar alcohol such as mannitol, glucose, molasses, etc., and the nitrogen source may include peptone, yeast extract or a combination thereof. The gel support may be selected from, for example, agar, and is not limited thereto. In some embodiments of the present disclosure, the culture medium may include agar, carbon source, peptone and yeast extract, wherein the weight ratio of the carbon source, peptone and yeast extract may be 5:1:1 to 4:1:1.

In at least one embodiment of the present disclosure, the fibrous membrane can be prepared by static fermentation of bacteria of the genus *Gluconobacter* in a culture medium comprising mannitol, peptone, yeast extract and agar, wherein the prepared fibrous membrane has a water content greater than 85%, such as greater than 90%, greater than 92% or greater than 95%.

In order to obtain fibers to be prepared for the prevention or treatment of diarrhea, constipation or irritable bowel syndrome, in at least one embodiment, the fibrous membrane is further subjected to a fiber separation procedure. The fiber separation procedure includes homogenizing pulverization of the fibrous membrane to obtain a dispersion, followed by swelling the interwoven biocellulose in the dispersion, and mechanical grinding of the swelled biocellulose.

As used herein, the term "homogeneous pulverization" refers to mixing a fibrous membrane with a solution, followed by use of a homogenizing device to pulverize with a fixed outer knife with shearing force and a saw-like and rotatable inner knife to prepare a dispersion.

In at least one embodiment of the present disclosure, after the dispersion is subjected to the aforementioned homogenous pulverization, other additives may be added to the dispersion to swell the interwoven biocellulose in the dispersion. The additives added in the present disclosure may include additives commonly used in the art, and are not limited thereto.

As used herein, the term "swelling" includes the penetration of the treatment liquid into the interwoven biocellulose in the dispersion to weaken the hydrogen bond between the cellulose, which does not lead to excessive hydrolysis of biocellulose and reduces the energy consumption in the subsequent mechanical grinding process. In some embodiments of the present disclosure, under the synergistic effect produced by the shearing force of the mechanical grinding, the glycosidic bonds of biocellulose are broken, thereby separating the biocellulose fibers. The specific surface area is thus increased with more exposed hydroxyl groups, thereby enhancing the hydrophilicity and biocompatibility of biocellulose.

In at least one embodiment, the treatment liquid of the present disclosure can be at least one selected from the group consisting of an alkali solution, an inorganic salt solution, and an ionic liquid aqueous solution. In some embodiments of the present disclosure, the base forming the alkaline solution includes at least one selected from the group consisting of potassium hydroxide, sodium hydroxide, and lithium hydroxide. In some embodiments of the present disclosure, the inorganic salt can be at least one selected from the group consisting of urea, zinc chloride, thiourea, calcium chloride and magnesium chloride. In some embodiments of the present disclosure, the ionic liquid can be at least one selected from the group consisting of 1-allyl-3-methylimidazolium chloride ([AMIm]Cl), 1-butyl-3-methylimidazolium chloride ([BMIm]C1), 1-allyl-3-methylimidazolium acetate ([AMIm]Ac), 1-butyl-3-methylimidazolium acetate, [BMIm]Ac), lithium chloride/dimethyl sulfoxide (LiCl/DMSO), N-alkylpyridines and di-alkylimidazoles.

As used herein, the term "mechanical grinding" includes diluting the dispersion with water and grinding with a horizontal ball mill to separate the interwoven biocellulose fiber in the dispersion to form fibers with a diameter of 15 nm to 35 nm and a length of 1.5 µm to 3.5 µm, wherein the amount of biocellulose used for mechanical grinding is between about 0.1% by weight and about 0.5% by weight of the total weight of the dispersion, such as about 0.15% by weight, about 0.2% by weight, about 0.25% by weight, about 0.3% by weight, about 0.35% by weight, about 0.4% by weight, or about 0.45% by weight. Thereafter, the swelled and mechanically ground dispersion is purified according to the conventional method, which includes neutralization and desalting, such as by dialysis using a semipermeable membrane to separate the salts in the dispersion to obtain the desired fiber.

In at least one embodiment of the present disclosure, the ground biocellulose has a high specific surface area which enhances the electrostatic effect, Van der Waals force or hydrogen bonding between the cellulose, which may facilitate agglomeration. Therefore, in some embodiments, the present disclosure may include further processing the ground dispersion liquid by ultrasonication after mechanical grinding to de-agglomerate the agglomerates of biocellulose, which can be optionally subjected to freeze-drying according to actual needs.

In at least one embodiment, the composition of the present disclosure may include fibers formed of β-1-4-glucan and other substances, wherein the fibers may be presented in the form of freeze-dried tablets or dry powder and combined with other substances to form the composition. In some embodiments, the composition of the present disclosure may further include at least one selected from the group consisting of organic nutrients, probiotics, drugs, dietary fibers, flavoring agents, dispersants, wetting agents, lubricants, thickeners, stabilizers, preservatives, antioxidants, antibacterial agents, and coloring agents, while there is no negative influence of these substances on the fibers of the present disclosure. In some embodiments, the fibers of the present disclosure exhibit a synergetic effect with the above-mentioned substances.

In at least one embodiment, the organic nutrient of the present disclosure includes an extract extracted from a culture medium of the static culture of the microorganism above. In some embodiments of the present disclosure, the flavoring agent includes a sweetener and/or flavoring. In some embodiments of the present disclosure, the probiotics include, for example, *Enterococcus, Lactobacillus, Bacillus, Clostridium, Lactococcus lactis, Leuconostoc, Pediococcus, Carnobacterium, Vagococcus, Tetragenococcus, Bifidobacterium, Atopobium, Weissella, Abiotrophia, Granulicatella, Oenococcus, Paralactobacillus* and *Saccharomyces boulardii* and any combination thereof. In some embodiments of the present disclosure, the probiotics may be selected from *Lactobacillus acidophilus, Lactobacillus casei, Lactobacillus reuteri, Bifidobacterium bifidum, Bifidobacterium lactis, Lactobacillus johnsonii, Lactobacillus paracasei, Lactobacillus rhamnosus, Bifidobacterium longum* and any combination thereof.

In at least one embodiment, the drug disclosed in the present disclosure may be a western medicine or a Chinese medicine, for example, a Chinese medicine or a western medicine clinically used for gastrointestinal diseases or a Chinese medicine or a western medicine that has the potential to be used as a medicine for the treatment of gastrointestinal diseases. For example, the traditional Chinese medicine can be Puerariae Lobatae Radix, raw hemp, *Scutellariae radix, Coptidis rhizoma, Phellodendri chinensis cortex, Atractylodis rhizoma, Pogostemonis herba, Amomi fructus*, poria, polyporus, *Coicis semen*, cinnamon, dried ginger, *Euodiae fructus*, pepper, *Atractylodis macrocephalae rhizoma, Dioscoreae rhizom*, lentils, *Psoraleae fructus, Fructus alpiniae oxyphyllae, Paeoniae radix alba, Schisandra chinensis, Mume fructus, Galla chinensis, Chebulae fructus, Myristicae semen, Nelumbinis semen, Euryales semen, Rosae laevigatae fructus, Chaenomelis fructus, Agastache* Qi-Righting Powder, *Pueraria coptis* & Scute Combination, Citrus & Cratagus Formula, Ginseng & Atractylodes Formula, "Tong Xie Yao Fang" (Important Formula for Painful Diarrhea), "Si Shen Wan" (Four Spirits Pill) and any combination thereof.

In some embodiments of the present disclosure, the fiber formed of β-1-4-glucan or a composition comprising the same can be administered when the symptoms are predicted to occur or before the symptoms occur, in order to achieve the effect of prevention and protection. For example, the composition of the present disclosure can be administered to individuals in need of prevention or treatment of diarrhea, constipation, or irritable bowel at a dose for 1 to 3 times a day, and each dose of freeze-dried tablet administered comprises 0.02 g to 0.12 g of the fiber. In some embodiments of the present disclosure, when the fiber formed of β-1-4-glucan is directly administered, it is administered 1 to 4 times a day to a subject in need of prevention or treatment of diarrhea, constipation or irritable bowel syndrome, and each administration comprises 0.02 grams to 0.12 grams of fibers.

In some embodiments of the present disclosure, the fiber formed of β-1-4-glucan or the composition comprising the same can be administered at the time or after the occurrence of the symptoms to relieve the symptoms. In some embodiments of the present disclosure, the route and form of administration are described above.

In at least one embodiment of the present disclosure, the fiber formed of β-1-4-glucan or a composition comprising the same can be taken orally twice a day to treat or relieve the aforementioned symptoms with an interval of 1 to 12 hours; for example, the interval can be 1 hour, 2 hours, 3 hours, 4 hours, 5 hours, 6 hours, 7 hours, 8 hours, 9 hours, 10 hours, 11 hours or 12 hours. In some embodiments of the present disclosure, the fiber formed of β-1-4-glucan or the composition comprising the same can be administered before a meal, after a meal, or before going to bed. In at least one embodiment, the fiber formed of β-1-4-glucan or the composition comprising the same can be orally administered three times a day at an interval of 4 to 8 hours. Optionally, the fiber or the composition may be administered more than 3 times a day, for example 4 times, until a more obvious relief symptom has been obtained.

The present disclosure is further explained in more detail by reference to the following embodiments; however, the embodiments are not intended to limit the scope of the present disclosure.

Test Subject

Subjects aged 21 to 50 years old, regardless of gender, with persistent gastrointestinal discomfort were recruited. Those diagnosed with irritable bowel syndrome by a physician according to Rome IV criteria were selected as the test subjects.

According to Rome IV criteria, functional gastrointestinal disorders (FGIDs) are classified based on organ location:
A. Esophageal disease;
A1. Functional chest pain;
A2. Functional heartburn;
A3. Reflux sensitivity;
A4. Globus;
A5. Functional dysphagia;
B. Gastroduodenal disease;
B1. Functional dyspepsia;
  B1a. Postprandial discomfort syndrome (PDS);
  B1b. Epigastric pain syndrome (EPS);
B2. Belching disorders;
  B2a. Excessive supragastric belching (from esophagus);
  B2b. Excessive gastric belching (from stomach);
B3. Nausea and vomiting disorders;
  B3a Chronic nausea vomiting syndrome (CNVS);
  B3b. Cyclic vomiting syndrome (CVS);
  B3c. Cannabinoid vomiting syndrome (CHS);
B4. Rumination syndrome;
C. Bowel disorders
C1. Irritable bowel syndrome (IBS); IBS with predominant constipation (IBS-C); IBS with predominant diarrhea (IBS-D); IBS with mixed habits (IBS-M); IBS unclassified (IBS-U);
C2. Functional constipation;
C3. Functional diarrhea;
C4. Functional abdominal bloating/distension;
C5. Unspecified functional bowel disorder;
C6. Opioid-induced constipation;
D. Centrally mediated disorders of gastrointestinal pain;
D1. Centrally mediated abdominal pain syndrome (CAPS);
D2. Narcotic bowel syndrome (NBS)/Opioid-induced gastrointestinal hyperalgesia;
E. Gallbladder and sphincter of Oddi disorders;
E1. Biliary pain;
  E1a. Functional gallbladder disorder;
  E1b. Functional biliary sphincter of Oddi disorder;
E2. Functional pancreatic sphincter of Oddi disorder;
F. Anorectal disorder;
F1. Fecal incontinence;
F2. Functional anorectal pain;
  F2a. Levator ani syndrome;
  F2b. Unspecified functional anorectal pain;
  F2c. Proctalgia *fugax;*
F3. Functional defecation disorder;
  F3a. Inadequate defecatory propulsion;
  F3b. Dyssynergic defecation.

The physician assesses whether the patient's gastrointestinal discomfort belongs to irritable bowel syndrome based on the symptoms that started at least six months ago, and that repeated abdominal pain occurred at least one day a week on average in the past three months, and are associated with more than two criteria in the following:

1. related to defecation, such as change in feeling of defecation, incomplete defecation or urgent defecation;
2. related to changes in the frequency of stool;
3. related to changes in form of stool, such as separated hard pieces, hard lumps or watery.

After other organic diseases were excluded (e.g., by methods such as medical history review, medication history, physical examination, stool test, blood test, endoscopy, X-ray, etc.) and if the above conditions were met, irritable bowel syndrome was diagnosed by a doctor. In addition, the symptoms of abdominal pain or abdominal discomfort can be relieved after defecation, and abdominal distension is also one of the auxiliary diagnosis factors of irritable bowel syndrome.

The classification of irritable bowel syndrome is as follows based on the Bristol stool form scale (BSFS) according to the hardness of stool:
  Irritable bowel syndrome with constipation (IBS-C): >25% of stools are hard stools and <25% are soft stools;
  Irritable bowel syndrome with diarrhea (IBS-D): >25% of stools are soft stools and <25% are hard stools;
  Mixed irritable bowel syndrome (IBS-M): >25% of stools are soft stools and >25% are hard stools; and
  Unclassified irritable bowel syndrome (IBS-U): those that cannot be classified into the above three types.

Among the patients, only those diagnosed with irritable bowel syndrome were recruited as the priority subjects to avoid other factors affecting the observation.

Example 1

Trial Method

Patients were to take 10 mL of the composition orally before lunch and dinner every day, where the composition comprises 0.2% by weight of fiber formed of β-1-4-glucan with the balance being water.

After the trial, a 7-point balanced scale was used by patients to answer the following questions: "Compared to the condition before entering the trial, how do you evaluate the relief of your symptoms of IBS, such as diarrhea, abdominal pain, bloating, persistent defecation impulse and frequency of defecation, proportion of soft stool, consistency of stool, incomplete defecation, and relief of other symptoms of IBS?" Effect of fibers formed of β-1-4-glucan was evaluated based on the patient's response to symptom relief.

7-Point Balance Scale:
Significant relief
Moderate relief
Slight relief
Unchanged
Slightly severe
Moderately severe
Significantly severe Among these, those who answered significant relief, moderate relief, and slight relief were considered as effective.

Subject 1

A 47-year-old man suffers from irritable bowel syndrome with diarrhea and has diarrhea three to four times a day. The patient underwent a 3-day trial. After the trial, the 7-point balance scale was used to answer the above questions and showed a significant relief. The subject reported that the diarrhea did not recur during the trial, and there was no diarrhea on the next day after the trial. The effect was excellent.

Subject 2

A 26-year-old female suffering from irritable bowel syndrome with constipation maintained a bowel movement once every 3 to 5 days after taking a stool softener prescribed by a doctor. The patient underwent a 7-day trial. After the trial, the 7-point balance scale was used to answer the above questions. The results showed that the symptoms were significantly relieved. During the trial, the subject could defecate once in the morning and once in the evening a day, and maintain smooth defecation on the next day after the trial.

Example 2

Trial Method

Patients were to take 10 mL of the composition orally at the time of symptom onset or before the onset of foreseeable symptom, where the composition comprises 0.2% by weight of fibers formed of β-1-4-glucan with the balance being water. After the trial, the patient answered the same question as in Example 1 on a 7-point balance scale to evaluate the symptom relief effect of the fibers formed of β-1-4-glucan based on the patient's answer.

Subject 3

A 34-year-old female suffers from unclassified irritable bowel syndrome and has frequent abdominal pain due to stress. When the symptoms of abdominal pain occurred, the patient took the above-mentioned composition orally, and answered the above-mentioned questions at least 1 hour later. The results showed that the symptoms of abdominal pain were significantly relieved, and the symptoms of abdominal pain were relieved within 5 to 10 minutes after oral administration.

Subject 4

A 36-year-old female suffers from unclassified irritable bowel syndrome, and often suffers from abdominal pain due to stress. When the symptoms of abdominal pain occurred, the patient took the above-mentioned composition orally, and answered the above-mentioned questions at least 1 hour later. The results also showed that the symptoms of abdominal pain were significantly relieved, and the symptoms of abdominal pain were relieved within 5 to 10 minutes after oral administration.

Subject 5

A 36-year-old male suffers from unclassified irritable bowel syndrome, with symptoms lasting for 6 years, especially diarrhea one day after drinking beer. The patient took the above composition orally 15 to 20 minutes before drinking alcohol. The patient answered the above questions at least one day after drinking, and the results showed a significant relief, that is, no diarrhea occurred. The patient continued the trial and drank alcohol for at least 5 times, with an interval of at least 3 to 6 days, and reported that the diarrhea symptoms were significantly relieved, and there was no diarrhea on the next day after drinking.

Example 3

Subject 6

A 50-year-old male suffers from irritable bowel syndrome with diarrhea daily, and the symptoms of diarrhea worsen when he felt stressed. The patient underwent a 3-day trial and took the above composition orally every day before going to bed and when the symptoms occurred during the day, i.e., twice a day. After the trial, the 7-point balance scale was used to answer the above questions. The results showed that the symptoms were significantly relieved and diarrhea symptoms did not appear during the 4-day period after the trial. The patient subsequently reported that the diarrhea symptoms recurred on the 5th day after the trial; however, after continuing to take the above composition twice a day in the above manner, diarrhea symptoms were not observed.

What is claimed is:

1. A method for treating irritable bowel syndrome in a subject in need thereof, the method comprising administering to the subject a composition including a fiber formed of β-1-4-glucan and a carrier thereof, wherein the fiber has a diameter of between 15 nm and 35 nm and a mean length of between 1.5 μm and 3.5 μm, wherein the fibers are formed by fermentation by at least one bacterium, wherein the irritable bowel syndrome is irritable bowel syndrome with constipation (IBS-C), irritable bowel syndrome with diarrhea (IBS-D), mixed irritable bowel syndrome (IBS-M), or unclassified irritable bowel syndrome (IBS-U).

2. The method of claim 1, wherein the fiber has a length-to-diameter ratio of from 60 to 150.

3. The method of claim 1, wherein the composition is administered to the subject at an effective amount for 1 to 4 times a day.

4. The method of claim 3, wherein the composition for each administration is a freeze-dried tablet including 0.02 g to 0.12 g of the fiber.

5. The method of claim 1, wherein the composition is administered to the subject in a form of fibers with a liquid medium.

6. The method of claim 5, wherein the liquid medium is water.

7. The method of claim 5, wherein the fiber is in a range of from 0.2% by weight to 1.2% by weight based on a total weight of the composition.

8. The method of claim 7, wherein the composition comprises 0.1 mL of water with $OD_{620}$ between 0.25 and 1.25.

9. The method of claim 8, wherein the $OD_{620}$ is between 0.4 and 1.22.

10. The method of claim 1, wherein the fiber is formed by fermentation by at least one bacterium selected from the group consisting of *Gluconacetobacter, Acetobacter, Rhizobium, Sarcina, Pseudomonas, Achromobacter, Alcaligenes, Enterobacter, Azotobacter* and *Agrobacterium*.

11. The method of claim 10, wherein the bacterium is at least one selected from the group consisting of *Acetobacter xylinum, Gluconacetobacter hansenii, Gluconacetobacter xylinus*, and *Gluconacetobacter sacchari*.

12. The method of claim 1, wherein the composition further includes at least one selected from the group consisting of an organic nutrient, a probiotic, a drug, a dietary fiber, a flavoring agent, a dispersing agent, a wetting agent, a lubricant, a thickening agent, a stabilizer, a preservative, an antioxidant, an antibacterial agent and a coloring agent.

13. The method of claim 1, wherein the composition is administered orally to the subject.

* * * * *